(12) United States Patent
Pfleiderer et al.

(10) Patent No.: US 10,286,196 B2
(45) Date of Patent: May 14, 2019

(54) DEVICE TO CONTROL MAGNETIC ROTOR OF A PROGRAMMABLE HYDROCEPHALUS VALVE

(71) Applicant: INTEGRA LIFESCIENCES SWITZERLAND SÀRL, Le Locle (CH)

(72) Inventors: Martin Pfleiderer, Auvernier (CH); Toralf Bork, Enges (CH)

(73) Assignee: INTEGRA LIFESCIENCES SWITZERLAND SÀRL, Le Locle (CH)

(*) Notice: Subject to any disclaimer, the term of this patent is extended or adjusted under 35 U.S.C. 154(b) by 306 days.

(21) Appl. No.: 15/198,757

(22) Filed: Jun. 30, 2016

(65) Prior Publication Data
US 2018/0001064 A1 Jan. 4, 2018

(51) Int. Cl.
| | | |
|---|---|---|
| *A61M 27/00* | (2006.01) | |
| *A61M 39/22* | (2006.01) | |
| *F16K 17/04* | (2006.01) | |
| *F16K 17/06* | (2006.01) | |
| *F16K 31/06* | (2006.01) | |
| *F16K 31/08* | (2006.01) | |

(52) U.S. Cl.
CPC .......... *A61M 27/006* (2013.01); *A61M 39/22* (2013.01); *F16K 17/0406* (2013.01); *F16K 17/0493* (2013.01); *F16K 17/06* (2013.01); *F16K 31/06* (2013.01); *F16K 31/088* (2013.01); *A61M 2039/226* (2013.01); *A61M 2250/00* (2013.01)

(58) Field of Classification Search
CPC .......... A61M 2039/226; A61M 27/006; A61M 39/22; F16K 31/06; F16K 17/0493; F16K 17/06; F16K 31/088
See application file for complete search history.

(56) References Cited

U.S. PATENT DOCUMENTS

| | | |
|---|---|---|
| 3,902,252 A | 9/1975 | Farber |
| 4,173,228 A | 11/1979 | Van Steenwyk et al. |
| 4,595,390 A | 6/1986 | Hakim et al. |
| 4,608,992 A | 9/1986 | Hakim et al. |
| 4,622,644 A | 11/1986 | Hansen |
| 4,839,809 A | 6/1989 | Leighton et al. |
| 5,309,096 A | 5/1994 | Hoegnelid |
| 5,425,382 A | 6/1995 | Golden et al. |
| 5,435,070 A | 7/1995 | Kilian |
| 5,438,990 A | 8/1995 | Wahlstrand et al. |
| 5,525,901 A | 6/1996 | Clymer et al. |
| 5,643,194 A | 7/1997 | Negre |
| 5,709,225 A | 1/1998 | Budgifvars et al. |
| 5,758,667 A | 6/1998 | Slettenmark |

(Continued)

*Primary Examiner* — Leslie R Deak
(74) *Attorney, Agent, or Firm* — Troutman Sanders LLP

(57) ABSTRACT

A setting adjustment tool for a magnetically adjustable device implanted in a patient includes a circumference. A plurality of magnetic coils can be circumferentially distributed on a circumference of the tool. One of the magnetic coils can be movable along the circumference between a plurality of predetermined positions associated with the selectable performance settings. The magnetic coils may also be capable of attracting or repulsing the at least one magnet of the rotor of the implanted device in a radial direction by at least a predetermined angle within a plane of rotation of an at least one magnet of the rotor thereby inducing a rotating moment into the rotor.

14 Claims, 16 Drawing Sheets

(56) References Cited

U.S. PATENT DOCUMENTS

| | | |
|---|---|---|
| 5,879,297 A | 3/1999 | Haynor et al. |
| 5,944,023 A | 8/1999 | Johnson et al. |
| 6,101,417 A | 8/2000 | Vogel et al. |
| 6,129,668 A | 10/2000 | Haynor et al. |
| 6,138,681 A | 10/2000 | Chen et al. |
| 6,216,028 B1 | 4/2001 | Haynor et al. |
| 6,230,038 B1 | 5/2001 | von Gutfeld et al. |
| 6,242,907 B1 | 6/2001 | Clymer et al. |
| 6,263,230 B1 | 7/2001 | Haynor et al. |
| 6,439,538 B1 | 8/2002 | Ito |
| 6,485,449 B2 | 11/2002 | Ito |
| 6,505,062 B1 | 1/2003 | Ritter et al. |
| 6,690,159 B2 | 2/2004 | Burreson et al. |
| 6,702,249 B2 | 3/2004 | Ito |
| 6,707,293 B2 | 3/2004 | Wan et al. |
| 6,882,146 B2 | 4/2005 | Maiwald |
| 6,891,367 B2 | 5/2005 | Shinmura et al. |
| 6,937,906 B2 | 8/2005 | Terry et al. |
| 7,126,331 B2 | 10/2006 | Johnson et al. |
| 7,173,419 B1 | 2/2007 | Johnson et al. |
| 7,197,354 B2 | 3/2007 | Sobe |
| 7,228,252 B2 | 6/2007 | Alexander et al. |
| 7,301,332 B2 | 11/2007 | Govari et al. |
| 7,334,582 B2 | 2/2008 | Bertrand et al. |
| 7,525,309 B2 | 4/2009 | Sherman et al. |
| 7,753,913 B2 | 7/2010 | Szakelyhidi, Jr. et al. |
| 7,842,004 B2 | 11/2010 | Kassem |
| 7,856,987 B2 | 12/2010 | Bertrand et al. |
| 8,015,977 B2 | 9/2011 | Bertrand et al. |
| 8,038,641 B2 | 10/2011 | Soares et al. |
| 8,089,276 B2 | 1/2012 | Kentsch |
| 8,148,978 B2 | 4/2012 | Sherman et al. |
| 8,241,240 B2 | 8/2012 | Murphy |
| 8,257,296 B2 | 9/2012 | Bertrand et al. |
| 8,398,617 B2 | 3/2013 | Ginggen et al. |
| 8,424,393 B1 | 4/2013 | Lee |
| 8,518,023 B2 | 8/2013 | Roth et al. |
| 8,539,956 B2 | 9/2013 | Bertrand et al. |
| 8,591,499 B2 | 11/2013 | Girardin et al. |
| 8,617,142 B2 | 12/2013 | Wilson et al. |
| 8,622,978 B2 | 1/2014 | Bertrand et al. |
| 8,630,695 B2 | 1/2014 | Negre et al. |
| 8,753,331 B2 | 6/2014 | Murphy |
| 8,836,458 B2 | 9/2014 | Lee |
| 8,862,200 B2 | 10/2014 | Sherman et al. |
| 9,149,615 B2 | 10/2015 | Wilson |
| 9,216,275 B2 | 12/2015 | Soares et al. |
| 9,220,876 B2 | 12/2015 | Girardin et al. |
| 9,242,077 B2 | 1/2016 | Wilson et al. |
| 2004/0017192 A1 | 1/2004 | Clymer et al. |
| 2004/0055610 A1 | 3/2004 | Forsell |
| 2004/0064030 A1 | 4/2004 | Forsell |
| 2004/0097803 A1 | 5/2004 | Panescu |
| 2004/0250820 A1 | 12/2004 | Forsell |
| 2006/0124140 A1 | 6/2006 | Forsell |
| 2007/0276218 A1 | 11/2007 | Yellen |
| 2008/0048635 A1 | 2/2008 | Hughes |
| 2008/0297145 A1 | 12/2008 | Mahr et al. |
| 2009/0275924 A1 | 11/2009 | Lattanzio et al. |
| 2010/0010338 A1 | 1/2010 | van Dam et al. |
| 2010/0292759 A1 | 11/2010 | Hahn et al. |
| 2011/0031961 A1 | 2/2011 | Durand et al. |
| 2011/0105992 A1 | 5/2011 | Girardin et al. |
| 2012/0041297 A1 | 2/2012 | McGary |
| 2012/0083856 A1 | 4/2012 | Thacker et al. |
| 2013/0245402 A1 | 9/2013 | Ziaie et al. |

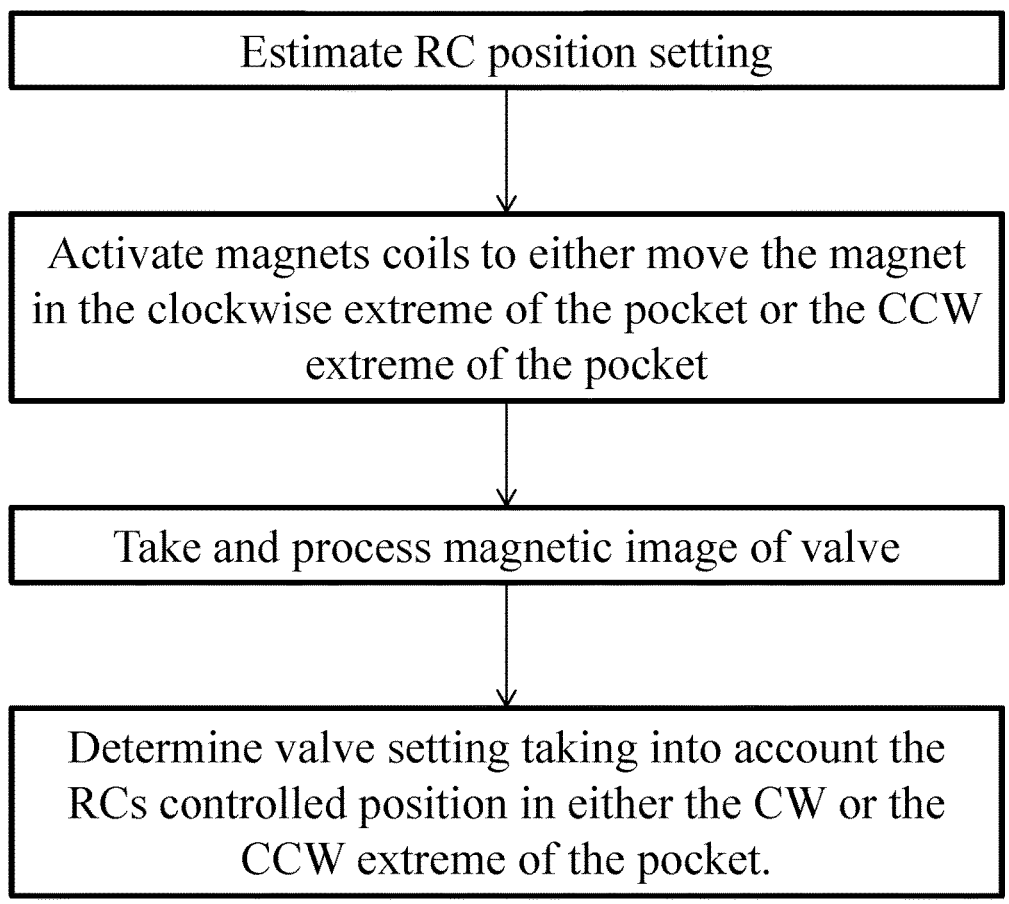

Fig. 23

Using a magnetoresistive sensor array to determine an approximate setting of valve 100 based on an approximate position of rotor 120, wherein rotor 120 may be between coils 776a and 774b or coils 774a and 772b

↓

Repulsing rotor 120 with coil 774a

↓

The magnetoresistive sensor array finding rotor 120 having moved only slightly, if at all

↓

Coil 774b repulsing rotor 120

↓

The magnetoresistive sensor array finding rotor 120 has moved clockwise towards coil 776a

↓

Coil 776a repulsing rotor 120

↓

The magnetoresistive sensor array finding rotor 120 has moved counter clockwise to coil 774b thereby positioning rotor 120 in a pocket between coils 774b and 776a

DEVICE TO CONTROL MAGNETIC ROTOR OF A PROGRAMMABLE HYDROCEPHALUS VALVE

FIELD

The present disclosure relates to techniques and tools to determine location, orientation and adjustment of implanted medical devices and more particularly to location, orientation and adjustment of adjustable valve mechanisms which resist unintentional performance setting changes.

BACKGROUND

There are a number of treatments for medical conditions which require fluid to be removed from an organ or tissue of a patient. One such condition is hydrocephalus, where cerebrospinal fluid abnormally accumulates in the skull faster than it is withdrawn by the body. The excessive build-up of cerebrospinal fluid compresses brain tissues, which eventually leads to brain damage.

Hydrocephalus is commonly treated by implanting a shunt in fluid communication with a ventricle within the brain to withdraw cerebrospinal fluid at a desired rate. Typically, the rate of withdrawal of cerebrospinal fluid is controlled by a valve having different pressure settings which a clinician adjusts pre-operatively.

A number of shunt valves can be noninvasively changed after implantation, such as the Codman® Hakim® programmable valve which is currently commercially available from Codman & Shurtleff, Inc. of Raynham, Mass. Other adjustable valves include the Strata™ valve from Medtronic Neurosurgery, the ProGAV™ valve manufactured by Christoph Meithke GMBH and distributed by Aesculap AG, and the Sophy™ and Polaris™ valves available from Sophysa USA Inc. All of these valves utilize applied magnet fields, such as those generated by magnets, to adjust valve pressure settings. To differing degrees, these valves are not optimal regarding resistance to unintentional setting changes, ease of use in achieving the desired valve setting, and detection of actual valve setting.

Techniques used to detect one or more parameters of such implanted device can include magnetic resonance imaging, also referred to as MRI. MRI is an increasingly common procedure for examining one or more regions of a patient and provides better contrast between tissue types than computed tomography and utilizes powerful magnetic fields instead of potentially harmful x-rays. While magnetic exposure levels from first generation MRI systems were typically up to 1.5 Tesla, newer MRI machines routinely use 3.0 Tesla. Such strong magnetic fields can, however, interfere with implanted devices including shunt valves.

As of the filing date for the present application, the Codman® CERTAS™ programmable valve is currently commercially available from Codman & Shurtleff, Inc. of Raynham, Mass. The CERTAS™ valve is generally resistant to MRI exposure up to at least 3.0 Tesla without unintentionally changing the valve setting. Intentional valve adjustment is accomplished using a suitably aligned magnetic field. Correct positioning of the applied magnetic field relies on the user.

It is therefore desirable to have simplified and more accurate techniques and tools to locate, determine orientation, and adjust implantable valves capable of withstanding strong magnetic fields and which resist unintended changes to valve settings. It is with respect to these and other considerations that the various embodiments described below are presented.

SUMMARY

In some aspects, the present disclosure relates to improved systems and methods to locate, determine orientation, and/or adjust as desired an implanted valve unit which resists unintentional performance setting changes when the unit is subjected to vibration, jarring or unintended magnetic fields. Such solutions may be capable of allowing one or more predetermined non-invasive changes to pressure or flow control settings of the implanted valve unit.

In some aspects, a method of adjusting a performance setting of a magnetically adjustable device implanted in a patient is disclosed. The device can include a housing with a rotor having an axis of rotation and at least one rotor magnet, the rotor having a range of arcuate motion within each of a plurality of selectable performance settings and the rotor can have an axle which turns about the axis of rotation. In this regard, the method includes: a magnetoresistive sensor estimating an approximate setting of the rotor of the device; activating a first magnet of a setting adjustment tool causing the at least one rotor magnet to move the rotor away from the first magnet; activating a second magnet of the setting adjustment tool causing the at least one rotor magnet to move the rotor next to the second magnet; activating a third magnet of the setting adjustment tool causing the at least one rotor magnet to move the rotor to a pocket of the device between second and third; imaging the device to produce an image of the device moved by the adjustment tool; and determining a performance setting of the device based on the image.

In certain embodiments, the pocket can be defined between one of a plurality of predetermined opposite lock stops of the housing associated with the selectable performance settings. The plurality of magnets of the adjustment tool may be magnetic coils circumferentially distributed about a circumference of the tool. Accordingly, each of the first, second, and third magnetic coils can be operable to radially attract or repulse the at least one rotor magnet. Two of the predetermined lock stops may be associated with the locks located at extreme counterclockwise and clockwise positions.

The plurality of magnets of the adjustment tool may be magnetic coils circumferentially distributed about a circumference of the tool. Each of the first, second, and third magnetic coils may be operable to radially attract or repulse the at least one rotor magnet. Activating the magnetic coils of the adjustment tool may also attract or repulse the at least one magnet of the rotor in a radial direction by at least a predetermined angle within a plane of rotation of the at least one magnet thereby inducing a rotating moment into the rotor.

One of the magnetic coils may be movable about the circumference. In this regard, the method can include moving the one of the magnets or magnetic coils between extreme counterclockwise and clockwise positions of the circumference thereby adjusting the device from a constrained condition setting to an unconstrained condition setting. At least one of the magnetic coils of the tool may also be movable about the circumference between a plurality of predetermined positions associated with performance settings of the device. The method may also include switching a magnetic polarity of the rotor by moving at least one of the magnetic coils between the plurality of predetermined positions to adjust opposite settings of the rotor.

The plurality of magnets of the adjustment tool may be magnetic coil pairs, each coil of each pair being angularly oriented together and circumferentially distributed about a circumference of the tool and relative to an associated lock stop of the housing. Each of the first, second, and third magnetic coil pairs may be operable to radially attract or repulse the at least one rotor magnet. Activating each magnetic coil pair of the adjustment tool thereby attracts or repulses the at least one magnet of the rotor in a radial direction by at least a predetermined angle within a plane of rotation of the at least one magnet thereby inducing a rotating moment into the rotor.

A predetermined angle may be formed between each coil of a respective coil pair (e.g. 45 degrees between each coil of the pair). One of the magnetic coils of the magnetic coil pairs or one of the magnetic coil pairs may also be movable such that moving the one of the magnet coils or magnetic coil pairs between extreme counterclockwise and clockwise positions of the circumference thereby adjusts the device from a constrained condition setting to an unconstrained condition setting.

The plurality of magnets can be circumferentially distributed equally on the circumference and/or the plurality of magnetic coils can be circumferentially distributed on a half of the circumference. However, the coils can be distributed about the entire circumference or less than half of the circumference or any other portion of the circumference as needed or required.

In other embodiments, a setting adjustment tool for a magnetically adjustable device implanted in a patient is disclosed including a circumference. A plurality of magnetic coils circumferentially distributed on the circumference (e.g. partially or completely about the circumference). Each magnetic coil may be operable to activate and attract or repulse the at least one rotor magnet. Any number of magnets and/or magnetic coils can be included as need or desired along or adjacent the circumference of the tool.

One of the magnetic coils may be movable between the extreme counterclockwise and clockwise positions and capable of adjusting the device from a constrained condition setting to an unconstrained condition setting.

One of the magnets or magnetic coils can be movable between the extreme counterclockwise and clockwise positions and capable of adjusting the device from a constrained condition setting to an unconstrained condition setting. Each magnetic coil can actually be formed by a pair of magnetic coils, each coil of each pair being angularly oriented together with respect to the other coil of the pair and circumferentially distributed about the circumference of the tool and relative to an associated lock stop of the housing.

The magnetic coils may be positioned on the circumference and be capable of attracting or repulsing the at least one magnet of the rotor in a radial direction by at least a predetermined angle within a plane of rotation of the at least one magnet thereby inducing a rotating moment into the rotor In other embodiments, a setting adjustment system for a magnetically adjustable device implanted in a patient. The system may include the magnetically adjustable device and a setting adjustment tool operatively connected to the magnetically adjustable device. The tool can include a circumference and a plurality of magnetic coils circumferentially distributed on the circumference. Each magnetic coil may be operable to activate and attract or repulse the at least one rotor magnet. At least one of the magnetic coils may be movable along the circumference between a plurality of predetermined positions associated with the selectable performance settings.

The plurality of magnetic coils may be magnetic coil pairs, each coil of each pair being angularly oriented together and circumferentially distributed about the circumference of the tool and relative to an associated lock stop of the housing. The tool may also include at least a first, second, and third magnetic coil pairs, each of the first, second, and third magnetic coil pairs being operable to radially attract or repulse the at least one rotor magnet. Activating each magnetic coil pair of the adjustment tool may attract or repulse the at least one magnet of the rotor in a radial direction by at least a predetermined angle within a plane of rotation of the at least one magnet thereby inducing a rotating moment into the rotor.

The coils in this embodiment can be circumferentially distributed on the circumference entirely or partially (e.g. on a half of the circumference). The plurality of magnets can include at least eight magnets equally distributed on the circumference and/or the plurality of magnetic coils can include at least eight coils equally distributed on the circumference (though any number of magnets and/or magnetic coils can be included as need or desired). At least one of the magnets or magnetic coils in the tool can be movable along the circumference between a plurality of predetermined positions associated with the selectable performance settings.

Other aspects and features of the present disclosure will become apparent to those of ordinary skill in the art, upon reviewing the following detailed description in conjunction with the accompanying figures.

BRIEF DESCRIPTION OF THE DRAWINGS

The herein disclosed solution is described with particularity in the appended claims. The above and further aspects of this solution may be better understood by referring to the following description in conjunction with the accompanying drawings, in which like numerals indicate like structural elements and features in various figures. The drawings are not necessarily to scale, emphasis instead being placed upon illustrating the principles of the solution. The drawing figures depict one or more implementations in accord with the present teachings, by way of example only, not by way of limitation. In the figures, like reference numerals refer to the same or similar elements.

Reference will now be made to the accompanying drawings, which are not necessarily drawn to scale.

FIG. 21 is a flow chart showing a method using one embodiment of the herein disclosed adjustment tool.

FIG. 23 is a flow chart showing a method of using an exemplary adjustment tool.

DETAILED DESCRIPTION

Figure 1:
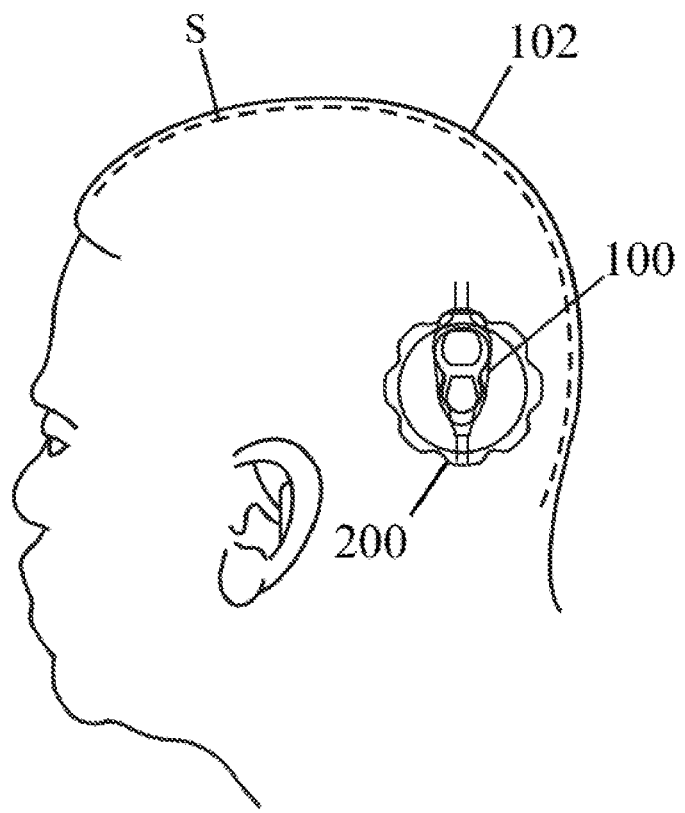
FIG. 1 is an illustration of a typical valve implanted in a patient.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways. It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" or "patient" may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braided stent body to the vasculature of a subject.

As discussed herein, "activate" may be understood as rendering something such as a magnet, a magnetic coil, and/or a pair of magnetic coils active or operative.

FIG. 1 depicts a generalized implantable valve 100 implanted beneath a patient's skin 102. The valve 100 includes a magnetic axis which is the point of reference used to adjust the valve 100. In an example, the valve 100 has a plurality of predetermined settings corresponding to a plurality of predetermined flows and pressures. In an example, the plurality of settings comprises eight settings. It is to be understood that the valve 100 can be any magnetically settable, implantable valve. The valve 100 can be adjusted or unlocked by placing a magnetic field over the magnetic axis. The attractive magnetic field for setting the valve can be provided by a single magnetic source that can be either a permanent magnet or an electromagnet.

The implanted valve unit 100 can include a rotor having an axis of rotation and at least one rotor magnet, the rotor having a range of arcuate motion within each of a plurality of selectable performance settings without altering a selected performance setting for the implanted device.

Turning back to the figures, FIG. 1 illustrates the valve 100 implanted under the skin 102 of a patient's skull S. Once implanted, the valve 100 is under the skin and typically covered by hair. Additionally, the area surrounding the valve may experience localized swelling, especially after surgery. Also, the patient may have a thin/thick scalp or small/large skull. Thus, a fixed foot can accommodate a range of sizes, while an adjustable foot accommodates a larger range, of bigger or smaller sizes.

Figure 2:
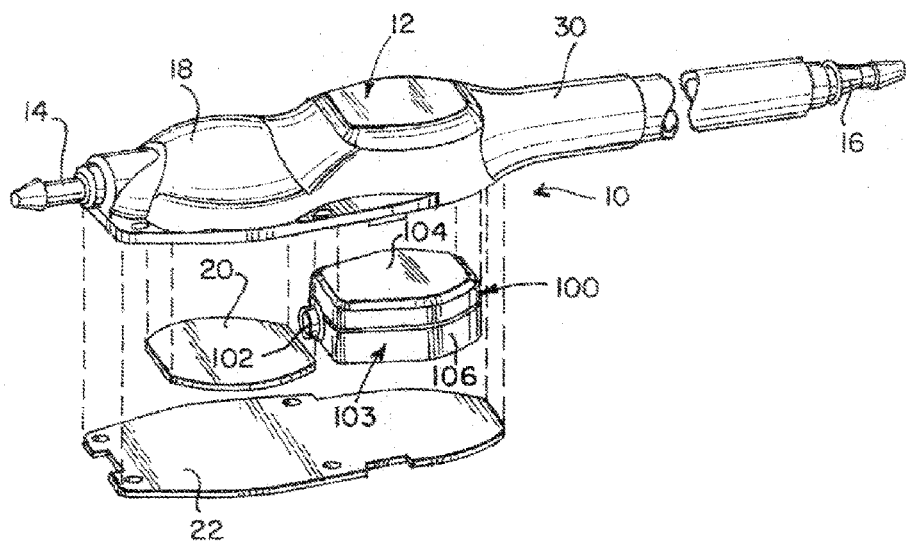
FIG. 2 is a schematic perspective exploded view of a novel programmable shunt valve device having an improved adjustable valve unit.

FIG. 2 illustrates a programmable shunt valve device 100 having a shunt housing 12, preferably formed of a translucent material such as silicone, with proximal connector 14 and distal connector 16. A ventricular catheter or other proximal catheter is connectable to connector 14 to bring fluid into shunt housing 12. Fluid passes into sampling or pumping chamber 18 and then through a valve mechanism in inlet 102 into novel adjustable valve unit 100, which is shown and described in more detail below. Valve unit 100 includes a casing 103 formed as upper casing 104 and lower casing 106 which are joined by sonic welding in this construction. A needle guard 20, preferably formed of a rigid polymeric material, and lower casing 106 are secured within housing 12 by a backing plate 22, preferably formed of silicone reinforced with a polymeric mesh, which is bonded to housing 12 by a medical grade epoxy.

When fluid pressure at inlet 102 exceeds a selected pressure setting within valve unit 100, fluid is admitted past a valve mechanism and then flows through valve unit outlet 110 into passage 30 of housing 12. Preferably, a Siphonguard® device, which is currently commercially available from Codman & Shurtleff, Inc. of Raynham, Mass., is disposed within passage 30. The Siphonguard® device (not shown) is designed to prevent excessive drainage of cerebrospinal fluid by a shunt system. One cause of excessive draining is a change in patient position from a supine to an upright position. Ultimately, fluid exits from housing 12 through distal connector 16 into a peritoneal catheter or other distal catheter.

Figure 3:
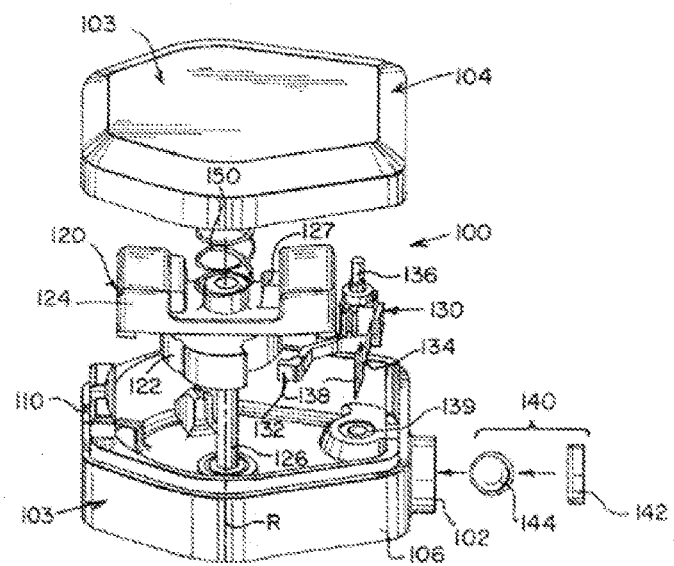
FIG. 3 is an exploded perspective view of the adjustable valve unit of FIG. 2.

Valve unit 100 of FIG. 3 can include rotor 120, spring arm unit 130, valve mechanism 140, and a rotor retention spring 150. In this construction rotor 120, also referred to as a rotating construct, is formed of a lower cam structure 122 having a plurality of radially flat cam surfaces, as shown and described in more detail below, and an upper, magnet housing 124 carrying magnetic elements 123 and 125. Housing 124 also defines a finger 127 which engages a stop in upper casing 104 when rotor 120 is moved to an unconstrained condition as described below. Rotor 120 rotates about axle 126 which defines a substantially fixed axis of rotation R at a first location in casing 103.

Preferably, rotor 120 is also capable of moving along the axis of rotation, in a translational motion, to an unconstrained condition when an adjuster tool is applied to it as described in more detail below. Retention spring 150 biases rotor 120 to a downward, normally constrained condition. Preferably, spring 150 is a coil spring having sufficient bias to resist the effect of gravity, regardless of the position of the valve unit, and to resist magnetic or ferrous objects, such as magnets in an indicator tool described in more detail below. However, spring 150 is insufficient to resist the effects of an adjuster tool, also described below. Lower cam section 122 has a sufficient height to ensure that cam follower 132 remains in contact with a cam surface in both the constrained and unconstrained conditions.

Spring arm unit 130 includes cam follower 132, a resilient spring element 134, and upper and lower axles 136 and 138 at a second location in casing 103. Axle 138 turns about a bearing 139 formed of a low-friction, hard material such as synthetic ruby. It is desirable for casing 103, rotor 120 and spring arm unit 130 to be formed of polyethersulfone, while all spring components are formed of medical grade non-ferromagnetic stainless steel.

Valve mechanism 140 includes seat 142 and movable valve member 144. Preferably, seat 142 and valve member 144, such as a ball, are formed of the same non-ferromagnetic material such as synthetic ruby. In other constructions, the movable valve member may be a disc, a cone, or other type of plug. A spherical ball is currently preferred because that shape enables tight, precise tolerances, assembly and control relative to the valve seat. Also, the position of the seat within a port can be adjusted during assembly of the valve unit to alter the actual performance value achieved at each setting, using a force versus displacement relationship. First, a mandrel checks the position of the ball, and the seat is inserted to an estimated desirable location within the port. Ball displacement is tested at one or more settings to confirm that desired performance will be achieved.

Figure 4:
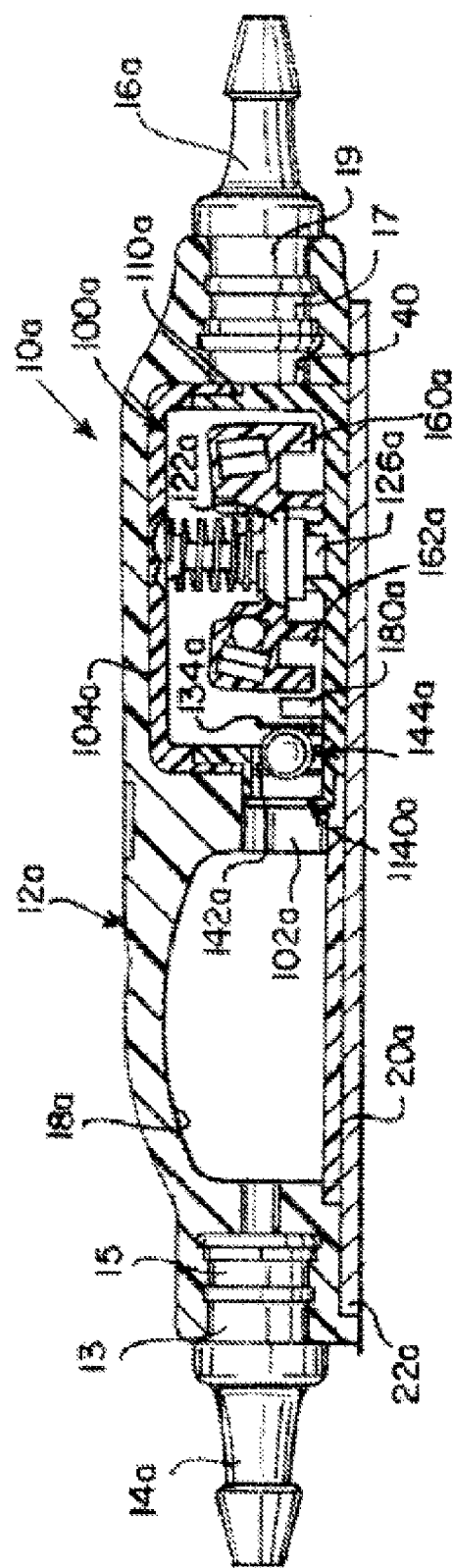
FIG. 4 is a side cross-sectional view of an alternative programmable shunt valve device having another novel adjustable valve unit.

Another shunt valve device 10a is shown in cross-section in FIG. 4 having a shunt housing 12a, proximal connector 14a with epoxy seals 13 and 15, and distal connector 16a with epoxy seals 17 and 19. Needle guard 20a and backing plate 22a form the floor of chamber 18a. Fluid flows into novel valve unit 100a through inlet 102a defined by lower casing 106a and exits through outlet 110a, defined by upper casing 104a in this construction, into a small chamber 40 and then directly into distal connector 16a.

Valve unit 100a may include a monolithic rotor 120a having pockets carrying magnetic elements 125a and 123a each having north N and south S magnetic orientations. Instead of a separate housing element which is molded independently and then attached to the lower rotor unit to form a combined rotor construct such as shown in FIGS. 2-3, rotor 120a is a different type of rotating construct that is micro-molded with pockets in the upper housing portion 124a of the rotor 120a together with lower cam portion 122a. Magnetic elements 123a, 125a and tantalum reference ball 129a then are placed in the pockets. Thereafter, epoxy such as Loctite® M-31™ epoxy is added to fill in remaining voids in the pockets to complete the rotor 120a. Axle 126a is shown as a separate component which is added to rotor 120a after it is removed from the micro-mold; in another construction, axle 126a is co-molded with the main rotor 120a. Also shown in FIG. 4 are rotor teeth 160a and 162a, movable valve element limiter 180a and a portion of spring element 134a pressing ball 144a against valve seat 142a. In an alternative construction, rotor teeth 160a, 162a are positioned below the cam portion 122a instead of projecting below the housing portion 124a as illustrated.

Figure 5:
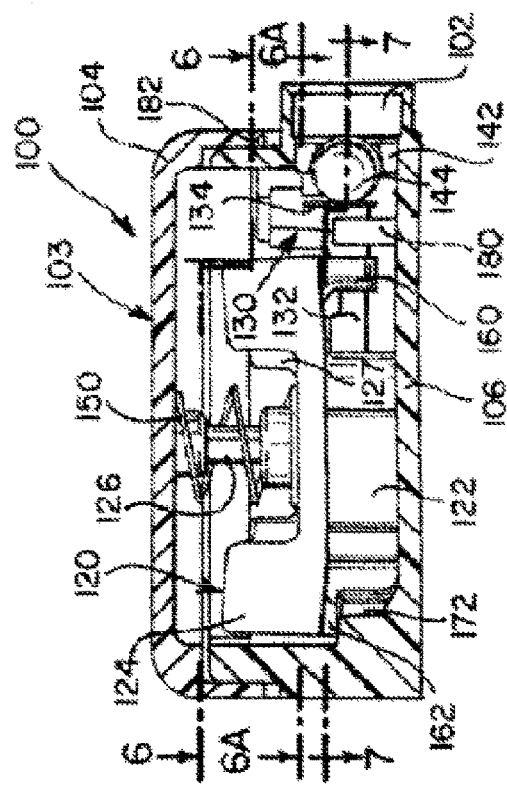
FIG. 5 is a top view of the adjustable valve unit of FIG. 2.
Figure 6:
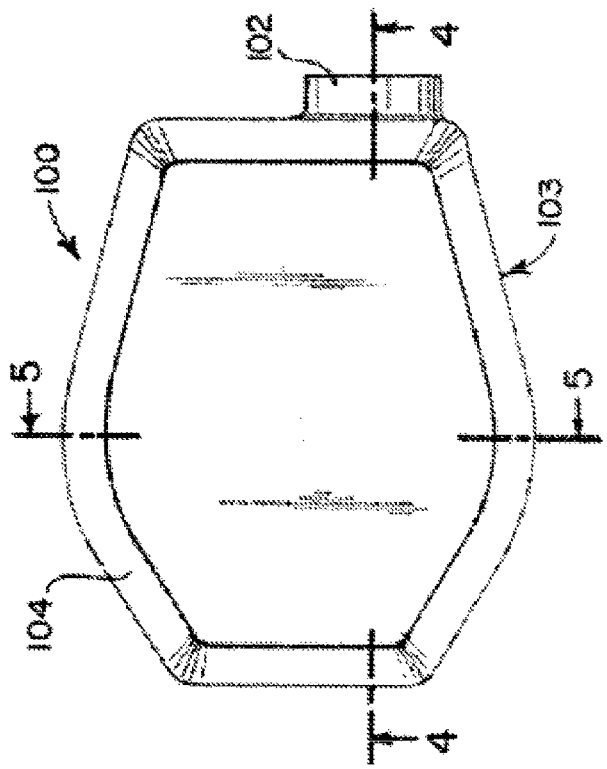
FIG. 6 is a side cross-sectional view of the adjustable valve unit of FIG. 5 along lines 4-4.

Valve unit 100 is shown assembled in FIGS. 5-6 and positioned at a second pressure setting, as described in more detail below. Specifically, FIG. 5 is a top view of valve unit 100 showing upper casing 104 of casing 103. Rotor housing 124 carries downwardly projecting teeth 160 and 162 with cooperate with four lock stops projecting upwardly from lower casing 106 in this construction. Lock stop 172 is shown in partial cross-section in FIG. 6 and lock stops 170 and 176 are visible in FIGS. 7-8. Preferably, the lower surfaces of rotor teeth 160 and 162 are rounded and the upper surfaces of casing lock stops 170, 172, 174 and 176 each have a plurality of facets to create a chisel-like, lead-in topography which encourages the rotor teeth to return to a constrained position. However, the vertical surfaces of teeth 160, 162 and of stops 170-176 abut when engaged and do not "lead out", that is, relative translational movement is discouraged. Pure vertical lift must be provided by an adjustment tool, as described in more detail below, to overcome the tooth-to-stop abutment and change the performance setting.

Figure 7:
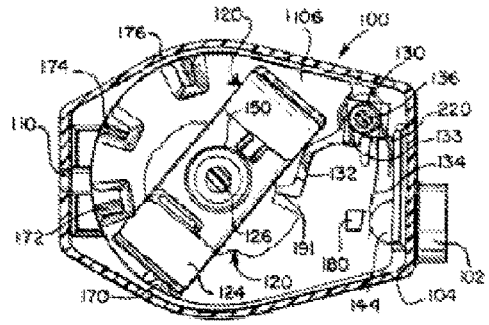
FIG. 7 is a partial cross-sectional view of the adjustable valve unit of FIG. 6 approximately along lines 6-6 at a first pressure setting.

A limiter 180 as shown in FIG. 7 restricts travel of spring 134 away from seat 142 so that ball 144 does not become misaligned or dislodged relative to seat 142. A gasket 182 of epoxy is shown in FIG. 6 as an optional, redundant seal between upper casing 104 and lower casing 106 in this construction.

Figure 7A:
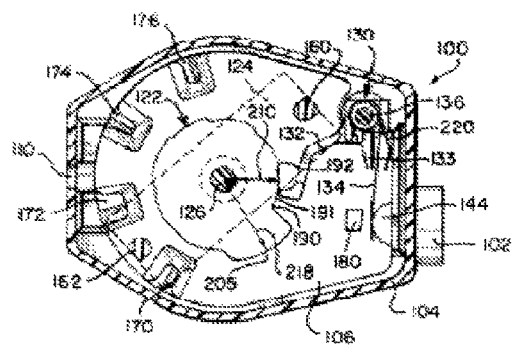
FIG. 7A is a deeper cross-sectional view of the adjustable valve unit of FIG. 6 approximately along lines 6A-6A at a first pressure setting.
Figure 7B:
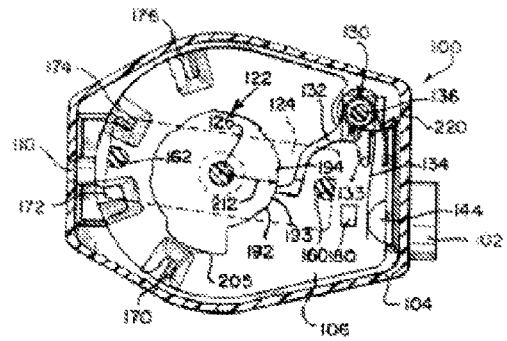
FIGS. 7B-7H are partial cross-sectional views of the adjustable valve unit of FIG. 6 at different, successive pressure settings.
Figure 8:
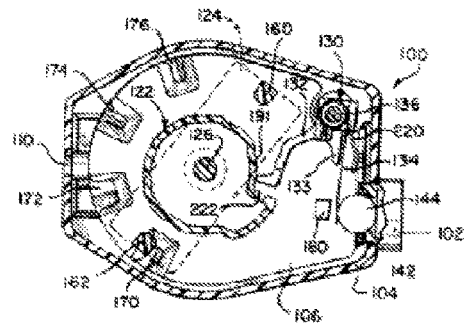
FIG. 8 is a deeper cross-sectional view of the adjustable valve unit of FIG. 6 approximately along lines 7-7.
Figure 9:
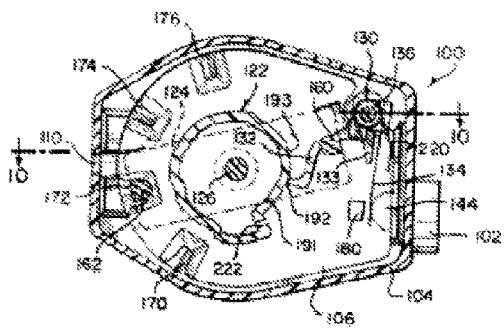
FIG. 9 is a cross-sectional view of the adjustable valve unit of FIG. 8 showing the transition to a different pressure setting.

The operation of valve units 100 and 100a are similar and are illustrated in FIGS. 7-9 in relation to valve unit 100, with identical reference numerals identifying identical components and features. Not all such components and features are labeled in each drawing for the sake of visual clarity. FIGS. 7 and 7A show different levels of top partial cross-sectional views for valve unit 100 at a first pressure setting. Cam follower 132 slidably contacts only a first cam surface 191, which has an arc length bounded by points 190 and 192, because rotor housing tooth 162 is captured between casing lock stops 170 and 172 in the normal, constrained condition. First cam surface 191 has a first, preferably shortest radial distance 210 relative to the axis of rotation of rotor 120. By comparison, outermost cam surface 205 has a greatest radial distance 218 as described in more detail below. An optional torsion spring 220 may also be used.

When rotor 120 is moved, (e.g. translated upwardly) by magnets in an adjustment tool as described below, rotor tooth 162 can be lifted so that subsequent clockwise or counter-clockwise rotation of the adjustment tool rotates tooth 162 up and over casing lock stop 172. After the adjustment tool is removed and when the second pressure setting has been selected as shown in FIG. 7A, rotor 120 is biased downwardly by spring 150.

Rotor tooth 160 is illustrated as not being in contact with any stop in FIGS. 5 and 7A, for example, because in the constrained condition rotor tooth 162 is now captured between a pair of lock stops 172 and 174, FIG. 7A, which is sufficient to prevent rotation of rotor 120 relative to the cam follower 132 beyond points 192 and 194 on the cam structure of rotor 120. Points 192 and 194 represent a second arc length for second cam surface 193. Surface 193 is at a second radial distance 212 which is greater than distance 210 and is less than distance 218, FIGS. 7A and 7H. The arc length of second cam surface 193, FIG. 7A, can be the same or different than the arc length of first cam surface 191 but, preferably, is substantially the same length.

The outward radial motion of cam follower 132 as it slidably travels from first cam surface 191, FIG. 7A, to second cam surface 193, FIG. 7A, increases the biasing force by valve spring 134 on ball 144 as increased torque is applied by cam follower 132 to the remainder of spring arm unit 130. Improved precision in pressure control is achieved by having a stiff cam follower 132 in contact with the selected cam surface and a flexible element, spring 134, in contact with the valve ball 144. The enhanced result is opening of the ball 144 from the valve seat 142 by requiring only the resilient spring element 134 to bend, which provides a constant spring force to the ball 144. The opening pressure, and overall valve performance, is not reliant on axial pivoting of the spring arm unit 130.

Figure 7C:
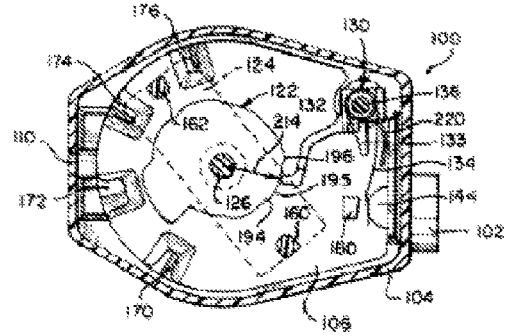
Figure 7D:
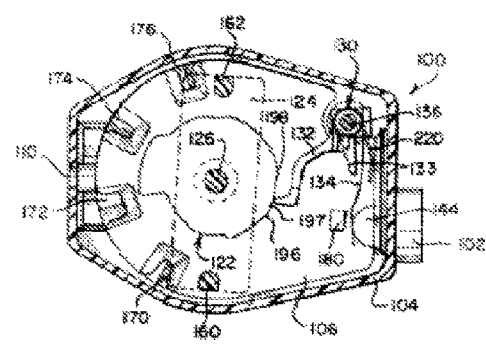

A third opening pressure setting is shown in FIG. 7C with rotor tooth 162 positioned between casing stops 174 and 176 such that cam follower 132 experiences only third cam surface 195 between points 194 and 196 at a third radial distance 214. To achieve a fourth pressure setting, FIG. 7D, both rotor teeth 160 and 162 are utilized relative to casing stops 170 and 176, respectively. Cam follower 132 is restricted thereby to fourth cam surface 197 between points 196 and 198.

Figure 7E:
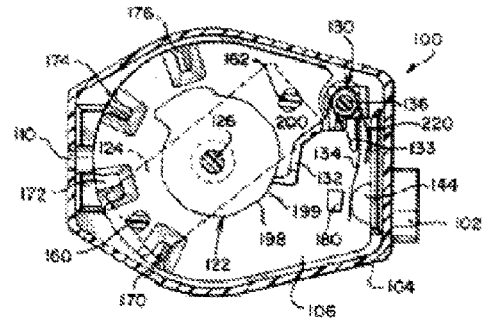
Figure 7F:
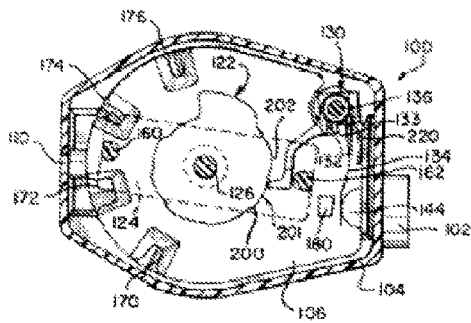
Figure 7G:
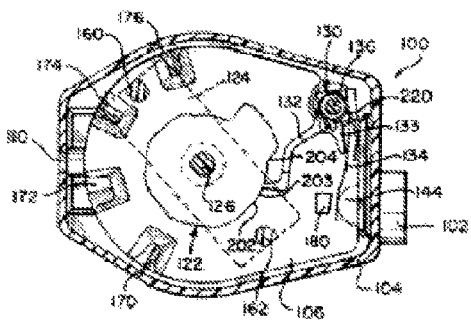

Fifth through seventh pressure settings are illustrated in FIGS. 7E-7G as rotor tooth 160 is successively captured between casing lock stop pairs 170-172, 172-174, and 174-176, respectively. Cam follower 132 is restricted thereby to fifth cam surface 199 between points 198 and 200, FIG. 7E, sixth cam surface 201 between points 200 and 202, FIG. 7F, and seventh cam surface 203 between points 202 and 204, FIG. 7G.

Preferred opening pressure settings currently range from approximately 30 mm to 210 mm water (294 Pa to 2,059 Pa) in seven increments of 30 mm (294 Pa), with a final, "virtual off" setting described in more detail below. Preferably, each valve unit is calibrated and tested at the time of manufacture at one or more flow rates. Actual opening pressure for each setting tends to vary according to flow rate, typically measured in milliliters per hour. Also, when tested with a 120 cm long distal catheter having an inner diameter of 1 mm, the average opening pressure typically will increase by 9 mm water or more at flow rates of 5 ml/h or more.

Figure 7H:
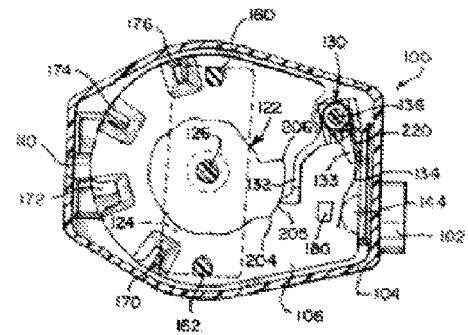

The final setting, FIG. 7H, of approximately at least 400 mm water (3,920 Pa) minimizes flow as a "virtual off" setting, that is, as substantially closed. This final setting is achieved by exposing cam follower 132 to outermost cam surface 205, defined by points 204 and 206, having greatest radial distance 218. This greatest cam setting forces stiffener element 133 of spring arm unit 130 against valve spring 134 to shorten its active, effective length and thereby dramatically increase the biasing force applied against ball 144. The final opening pressure is increased by more than fifty percent over the prior setting. In other constructions, a stiffener element is forced against a valve spring during two or more final cam settings at desired pressure increments.

Use of torsion spring 220 is optional, and is possible because only spring element 134 contacts the movable valve member. As a result, additional spring force from torsion spring 220 can be utilized to force bearing surface 235 of cam follower 132 against a cam surface of the rotor. This biasing force provided by torsion spring 220 augments rotational position of the spring arm reflective of the intended cam displacement without otherwise impacting the force applied to the ball or other movable valve member. This provides for a more accurate and repeatable opening pressure and a more manufacturable and robust design as it reduces the need to maintain minimal friction such as when the valve spring element solely provides the force needed to maintain the cam follower on the cam surface.

The position of the components and features within valve unit 100 at the first pressure setting shown in FIG. 7A is illustrated at a deeper partial cross-sectional view in FIG. 8. Opening 222 into the lower cam portion of rotor 120 inhibits negative pressure from developing under rotor 120, that is, opening 222 ensures pressure equalization as cerebrospinal fluid passes through valve unit 100.

The transition from the first pressure setting to the second pressure setting is illustrated in FIG. 9 as rotor 120 is translated upwardly by magnetic attraction with an adjustment tool so that rotor tooth 162 is able to clear casing lock stop 172. Cam follower 132 is shown in FIG. 9 at point 192 passing from first cam surface 191 to second cam surface 193. Lower cam section 122 has a sufficient height relative to cam follower bearing surface 235 to ensure that cam follower 132 remains in contact with a cam surface of cam portion 122 in both the constrained and unconstrained conditions. Rotor retention spring 150 has been compressed, its biasing force being overcome by magnetic attraction between rotor 120 and the adjustment tool while it is positioned over valve unit 100.

The position of the components and features within valve unit 100 at the final, "virtual off" or substantially closed setting shown in FIG. 7H. Further clockwise rotation of rotor 120 is prevented by rotation stop or limiter 250 which projects downwardly from upper casing 104 to contact finger 127. Rotation stop 250 contacts the opposite surface of finger 127 when rotor 120 is turned fully counterclockwise in an unconstrained condition. The actual position of rotation stop 250 may be shifted to the right of the position so that cam follower 132 is able to track nearly the entire portion of cam surface 205. Preferably, one side of stop 250 prevents rotor movement from the lowest setting directly to the highest setting, and also prevents the cam follower from touching the cam projection for the highest setting when the rotor is at its lowest setting. The other side of stop 250 prevents movement from the highest setting directly to the lowest setting.

In a preferred construction, unintentional setting changes are minimized by the combination of (a) a substantially fixed, tight-tolerance, non-wobbling rotor axle, (b) abutting rotor-tooth-to-casing-stop vertical surfaces as described above, (c) a spring which biases the rotor toward the constrained condition as described above, and (d) off-axis magnets within the rotor which tend to bind the axle when a magnetic field is applied to the valve unit. In other words, it is preferable to configure the valve unit components to limit the allowable plane(s) of motion and to restrict translational movement of the rotor. The axis of magnetization of the rotor magnets preferably are arranged to lie between forty-five degrees to ninety degrees relative to the axis of rotation of the rotor, more preferably between seventy-five to eighty-five degrees. It is also preferable to orient the north and south poles of each magnet as described in more detail below.

Figure 10:
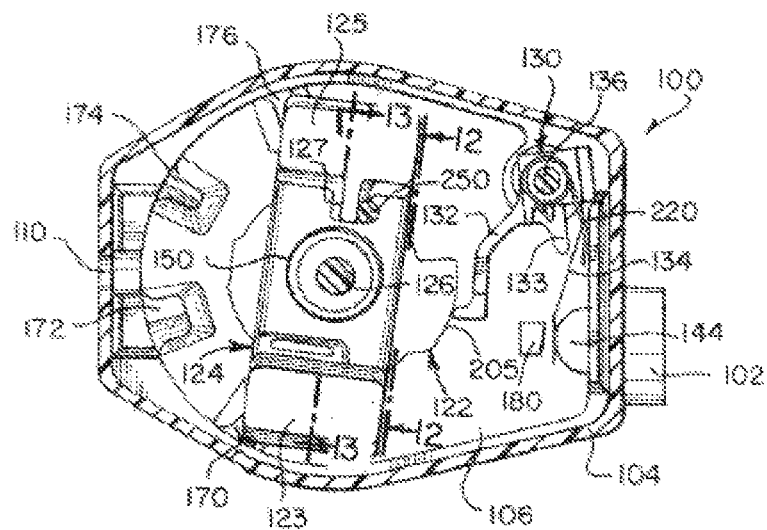
FIG. 10 is a partial top cross-sectional view of the adjustable valve unit of FIG. 7H showing the "virtual off" position in an unconstrained condition.

It is desirable for the magnets 123 and 125 in the rotor 120 to be block or slot shape magnets that are magnetized through thickness, that is, each of magnets 123 and 125, preferably include an axis of magnetization perpendicular to its length and width, and is arranged with north-south polarity orientation. For the construction shown in FIG. 10, magnets 123 and 125 have $BH_{max}$ of approximately 35 MGOe, with a length of 2.45 mm, a width of 1.45 mm and a thickness of 1 mm. The term $BH_{max}$ refers to the maximum energy product of a magnetic material, which is the magnetic field strength at the point of full saturation of the magnetic material measured in mega gauss oersteds. Magnets 450 and 452 in a corresponding adjustment tool 306, may be axially magnetized, disc shaped magnets with a diameter of 15.9 mm and a height of 15.9 mm. Suitable material, which resists demagnetization at fields up to three Tesla, for valve unit magnets includes NdFeB, and suitable material for adjustment tool magnets includes NdFeB grade 42-52.

Figure 11:
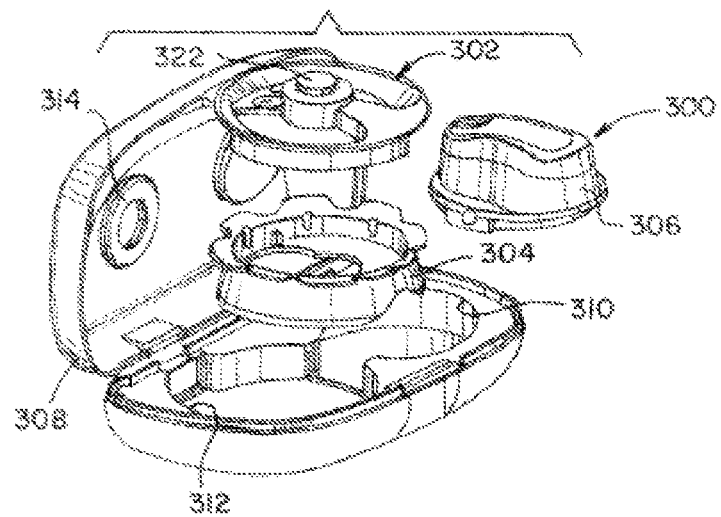
FIG. 11 is a perspective view of one embodiment of a tool set according to the present solution including an indicator tool, a locator tool, and a setting adjuster tool.

Toolset 300 can include one or more of any of the herein disclosed adjuster tools such as tool 306 and the one or more tools can be nestable on top of a locator tool as shown and described in more detail below. As illustrated in FIG. 11, a transport case 308 may have a smaller recess 310 for carrying adjuster 306 and a larger recess 312 for carrying indicator 302 nested with locator 304. Preferably, indicator release button 322 of indicator 302 is received within upper recess 314 when case 308 is closed for storage or transport of toolset 300.

Various adjustment tools are shown in FIGS. 11-15 that can be positioned so that, for example, an arrow 438 is aligned with the current valve setting, which is not necessarily aligned with a locator marking. As shown and described more particularly below, the clinician can move one or more magnets or coils of the adjustment tool until achieving the desired valve setting. After the desired setting is reached, adjustment tool can be lifted directly away from valve unit 100 without further rotation. The implanted valve unit 100 can be imaged with any manner desirable, for example, x-ray to determine the performance setting associated with valve 10.

Figure 12:
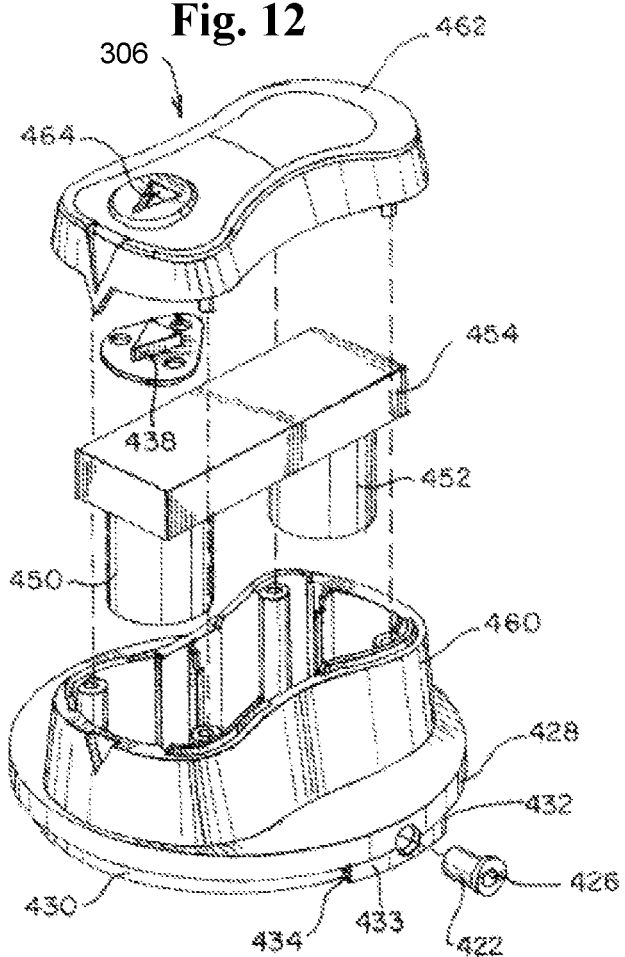
FIG. 12 is an exploded view of the setting adjuster tool for use with any of the disclosed adjustable valve units.

Turning to FIG. 12, components of an adjustment tool 306 include a metal yoke 454, such as a bar of 416SS stainless steel, for supporting magnets 450 and 452 in a housing 460. Preferably, the poles of the magnets are aligned so that one magnet has a "north" polarity at its base while the other has an opposite, "south" polarity at its base. A cover 462 defines an opening 464 which receives arrow marker 438 in this construction as shown in FIG. 12; in other constructions, marker 438 is integral with cover 462 or is applied to its surface after molding.

Figure 13:
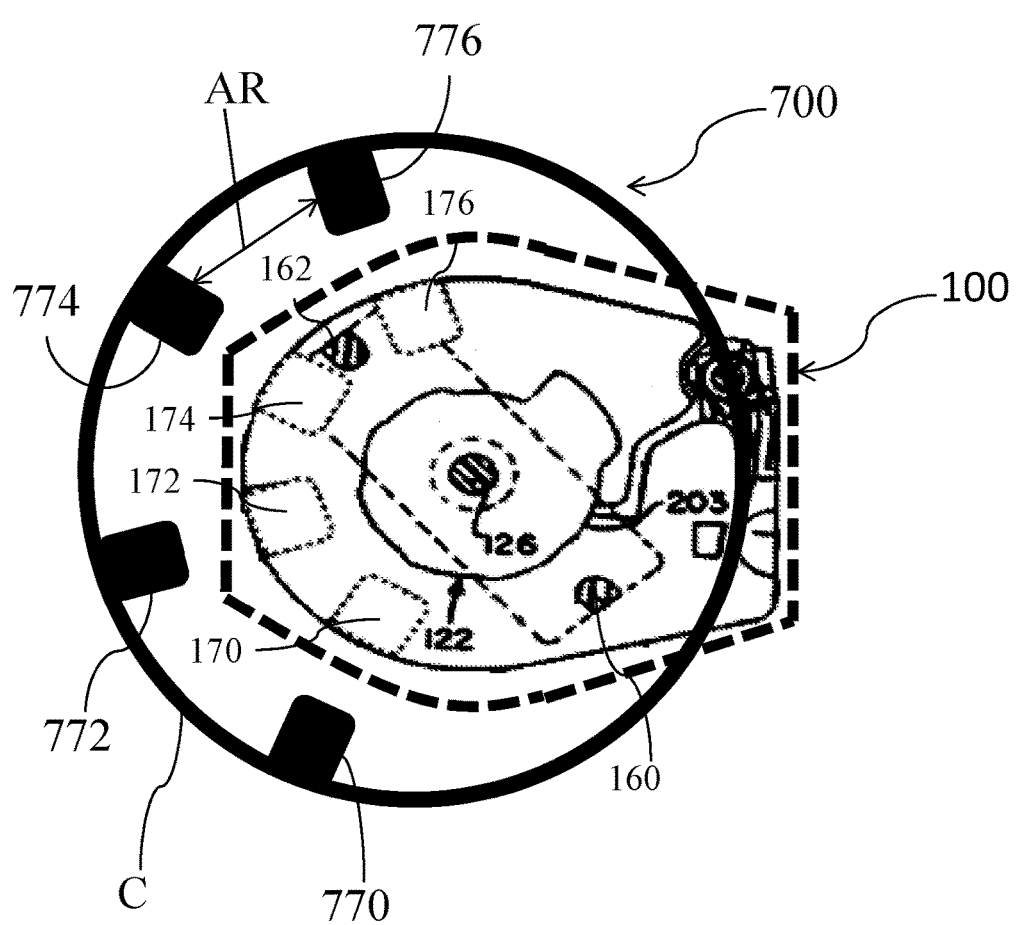
FIG. 13 is a top plan view of an exemplary adjuster tool assembled over an adjustable valve unit.

Another exemplary adjuster tool 700 is shown in a top plan view in FIG. 13 assembled over valve unit 100. Specifically, adjuster tool 700 is operable to control rotor 120 of valve unit 100 by attraction or repulsion. Tool 700 may include a plurality of circumferentially distributed magnets and/or magnetic coils 770, 772, 774, 776 positioned on or in the circumference C of tool 700 for moving rotor 120 inside its setting pocket (e.g. between stops 170, 172, 174, 176) to a predetermined position and thus adjusting the valve setting associated with rotor 120. For example, each magnet and/or magnetic coil 770, 772, 774, 776 can be separated an angular range AR (e.g. about 40 to 50 mm) though any range AR can be used as needed or required. In a non-limiting example, at least eight magnets and/or coils can be equally distributed on the full circumference C. However, the tool 700 is not so limited and at least four coils can be equally distributed on half of the circumference C as shown in FIG. 13. One magnet and/or magnetic coil of tool 700 can be moved along the circumference C into one of a plurality of defined positions.

In this respect, circumference C of tool 700 may be defined by a circular or elliptical cover with a circumference to move rotor 120. For example, relative angles between two different valve settings of previously known implanted valves can be as low as 8.5 degrees. As a consequence the flow direction of the valve must be known to the user (or be determined by any suitable device) with an accuracy of approximately four degrees in order to reliably read the valve setting. Tool 700 is capable of resolving this by moving the rotor 120 inside its setting pocket to a defined position in order to eliminate the need for an accurate determination of valve 10's flow direction during valve programmation. This in turn will allow for a very reliable determination of the current valve setting and setting change even with instruments of limited accuracy.

The magnets and/or coils of tool 700 may be operable to attract or repulse the magnets of the rotor 120 in a direction that is inclined to the radial direction by a predetermined angle (e.g. at least 45 degrees within the plane of RC rotation) in order to induce a rotating moment into rotor 120. This is particularly advantageous with the magnetic coils 770, 772, 774, 776 since the magnetic polarity of the coils 770, 772, 774, 776 can be switched in order to accommodate opposite positions of rotor 120.

A method of using tool 700 to reliably determine a valve setting of valve 10 is shown in FIG. 21 and includes the following steps: estimating a rotor position of the valve, activating coils or magnets of an adjuster tool and moving a magnet and/or coil of the adjuster tool that is movably positioned on a perimeter or circumference of the tool, imaging the valve and rotor position, and then determining a valve setting taking account the rotor controlled position in either the clockwise or counter clockwise extreme of the respective pocket. The method can further include moving the rotor in a first arcuate direction and detecting a first limit of travel without altering the current performance setting, moving the rotor in a second, opposite direction and detecting a second limit of travel without altering the current performance setting, comparing the first and second limits of travel with known values for the plurality of selectable performance settings, and indicating the current performance setting of the implanted device.

Figure 22:
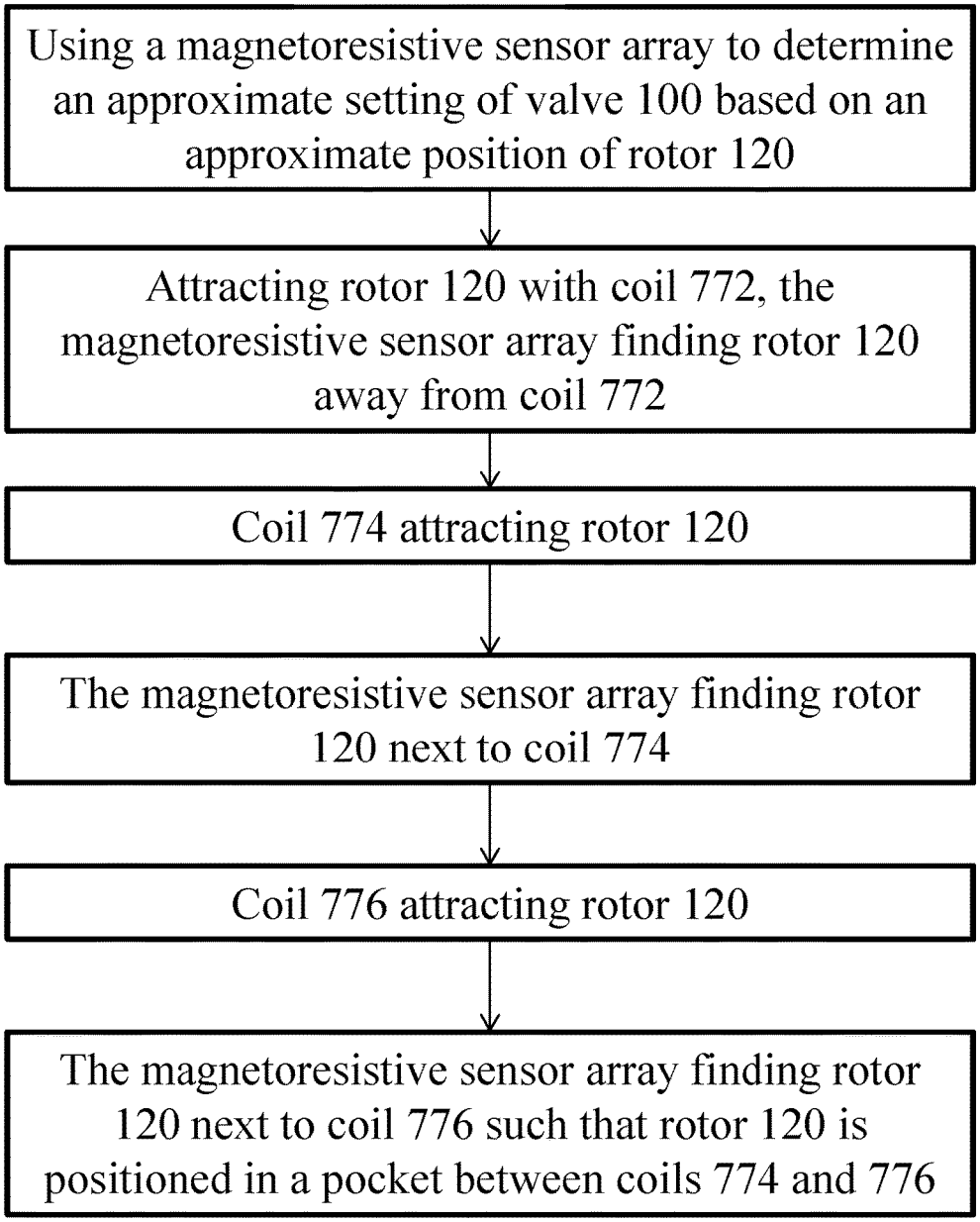
FIG. 22 is a flow chart showing a method of using an exemplary adjustment tool.

Another method of using tool 700 is shown in a flow chart of FIG. 22 including: using a magnetoresistive sensor array to determine an approximate setting of valve 100 based on an approximate position of rotor 120; attracting (or repulsing) rotor 120 with coil 772, the magnetoresistive sensor array finding rotor 120 away from coil 772; coil 774 attracting (or repulsing) rotor 120; the magnetoresistive sensor array finding rotor 120 next to coil 774; coil 776 attracting (or repulsing) rotor 120; the magnetoresistive sensor array finding rotor 120 next to coil 776 such that rotor 120 is reliably positioned in a pocket between coils 774 and 776. Advantageously, the respective valve setting of valve 10 is now reliably known.

Figure 14:
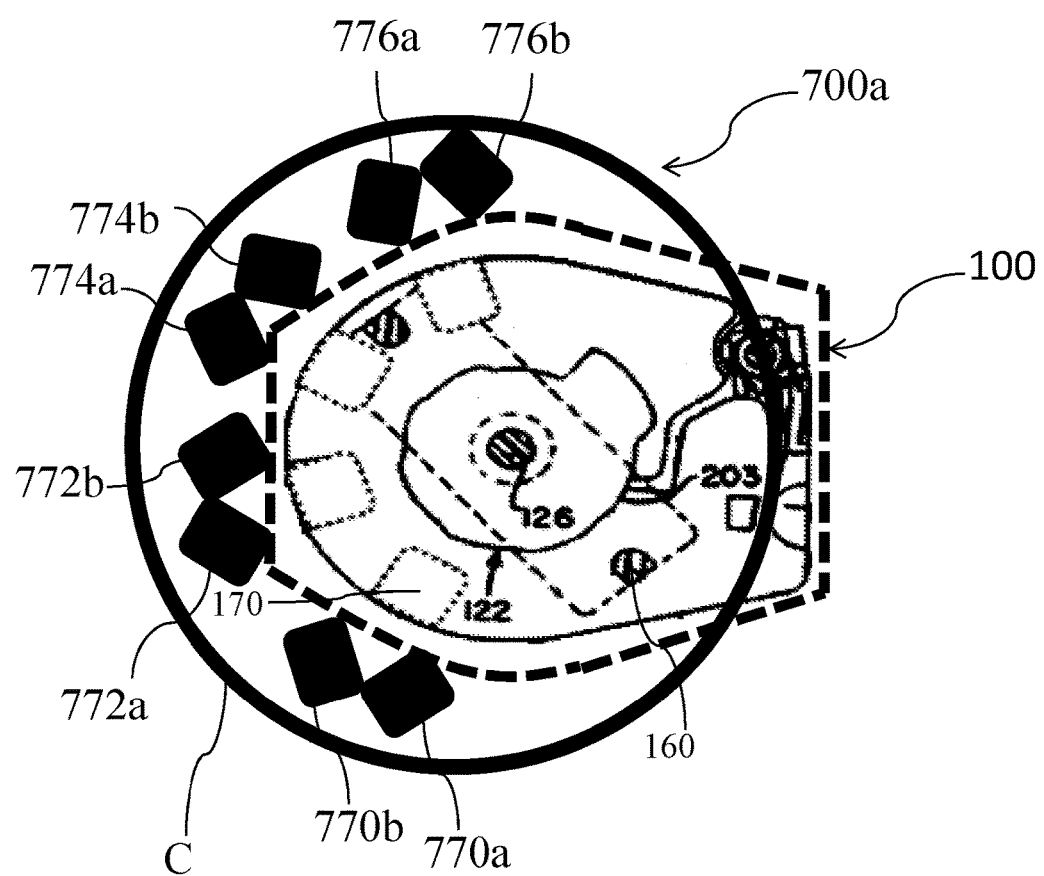
FIG. 14 is a top plan view of another exemplary adjuster tool assembled over an adjustable valve unit.

Another exemplary adjuster tool 700a is shown in a top plan view in FIG. 14 assembled over valve unit 100. Specifically, adjuster tool 700a is operable to control rotor 120 of valve unit 100 by attraction or repulsion. Tool 700a may include a plurality of circumferentially and/or angularly distributed magnets and/or magnetic coil pairs 770a and 770b, 772a and 772b, 774a and 774b, and 776a and 776b positioned on or in the circumference C of tool 700 for moving rotor 120 inside its setting pocket (e.g. between stops 170, 172, 174, 176) to a predetermined position and thus adjusting the valve setting associated with rotor 120.

As can be seen, each coil pair of tool 700a can be selectively angled at a predetermined angle (e.g. 45 degrees relative to each adjoining edge of respective coil) and disposed on or adjacent circumference C to magnetically communicate with rotor 120. In a non-limiting example, at least four coil pairs can be equally distributed on a half-circumference of circumference C. However, the tool 700a is not so limited and fewer or greater number of coil pairs can be equally distributed on half of the circumference as shown in FIG. 14 or throughout most, if not all, of circumference C. Additionally, one coil or one coil pair of tool 700a can be moved along the circumference C into one of a plurality of defined positions.

A method of using tool 700a to reliably determine a valve setting is shown in a flow chart of FIG. 23 including: using a magnetoresistive sensor array to determine an approximate setting of valve 100 based on an approximate position of rotor 120 (e.g. rotor 120 may be between coils 776a and 774b or coils 774a and 772b); repulsing rotor 120 with coil 774a; the magnetoresistive sensor array finding rotor 120 having moved only slightly, if at all; coil 774b repulsing rotor 120; the magnetoresistive sensor array finding rotor 120 has moved clockwise towards coil 776a; coil 776a repulsing rotor 120; the magnetoresistive sensor array finding rotor 120 has moved counter clockwise to coil 774b thereby positioning rotor 120 in a pocket between coils 774b and 776a. Advantageously, the respective valve setting of valve 10 is now reliably known.

Additionally, when using tool 700a or tool 700, repulsion can be used for moving rotor 120 if the magnet or respective coil is positioned above the plane of the RC rotation in order to safely avoid unlocking of an MRI lock of valve 10. As a result of the RC manipulation within the pocket the relative RC angle between two adjacent, settings will be 45 degree approximately. Any systems and methods to read the valve setting of unit 100 in this regard require the flow direction to be determined with an accuracy of 20 degree only rather than 4 degree. Advantageously, tools 700 and 700a being operable to subsequently adjust the rotor 120 to a desired setting causes the required accuracy to increase from approximately 20 to 16 degree.

Figure 15:
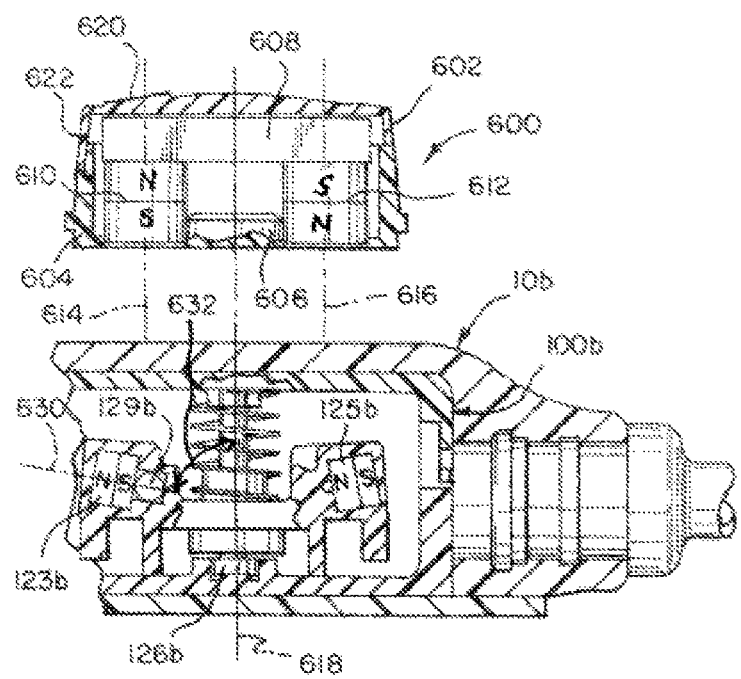
FIG. 15 is a schematic cross-sectional view along a center line of an adjuster tool.

Another adjuster tool 600 is shown in FIG. 15 positioned over skin of a patient with an implanted shunt valve 10b having a valve unit 100b, which is similar in construction to shunt valve 10 with valve unit 100 as shown and described above relative to FIG. 3.

Adjuster tool 600 has an upper housing 602 and a lower housing 604 with an enlarged floor portion 606 to assist securing magnets 610 and 612 in position. Upper casing 602 has an integral directional arrow 620 for proper alignment with a locator tool and has a marker 622 which confirms directional alignment of upper casing 602 with lower casing 604 during assembly. Adjuster magnets 610 and 612 are connected by metal yoke 608 and each has an axis of magnetization 614 and 616, respectively, which are substantially parallel in this construction as indicated with dashed lines. During adjustment of a valve unit according to the present solution such as valve unit 100b, axes of magnetization 614 and 616 are oriented to be substantially parallel to axis of rotation 618 through axle 126b of rotor 120b. In this construction, adjuster magnet 610 has a south pole S that is oriented to face rotor magnet 123b and imaging reference ball 129b while north pole N of magnet 612 is oriented to face rotor magnet 125b. Rotor 120b is shown in a constrained condition in FIG. 15, and is lifted to an unconstrained condition when the lower surface of adjuster tool 600 approaches within three cm (less than 1.25 inches) of the floor of a locator tool positioned on skin SK.

Axis of magnetization 630 of rotor magnet 123b is shown having an angle 632 relative to axis of rotation 618, with north pole N facing radially outwardly relative to axis of rotation 618. Rotor magnet 125b has a similar axis of magnetization, but with south pole S facing radially outwardly away from axis of rotation 618. Angle 632 is approximately eighty degrees in this construction. While an angle of ninety degrees from axis of rotation 618 for the axes of magnetization for rotor magnets 123b and 125b may be most effective for detection of actual setting by an indicator tool according to the present solution, it has been found that offset angles of seventy-five to eighty-five degrees, most preferably approximately eighty degrees, are suitable for interaction with the adjustment tool 600. Further, having axes of magnetization other than zero degrees and ninety degrees reduces the likelihood of simultaneous de-magnetization of embodiments with multiple rotor magnets when exposed to a magnetic field greater than 3 Tesla or other large electromagnetic field. In other words, it is preferable for the axes of magnetization of the rotor magnets to be offset relative to each other instead of parallel to each other to resist de-magnetization as well as to encourage binding of axle 126b when exposed to unintended magnetic fields.

Figure 16:
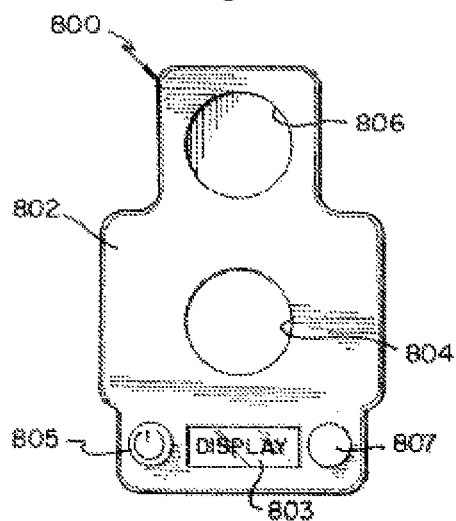
FIGS. 16 and 16A are schematic top and side views of a positioning tool of a positioning toolset according to the present invention.
Figure 16A:
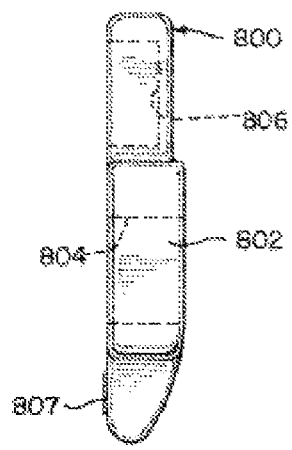
Figure 18:
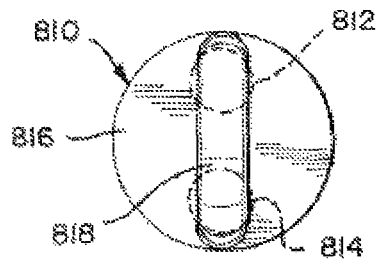
FIGS. 18 and 18A are schematic top and side views of an adjustment tool for use with the positioning tools of FIGS. 16 and 17.
Figure 18A:
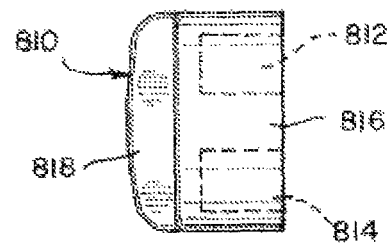

In many circumstances, it is desirable to decrease reliance on the accuracy of a user while positioning the tool set and to increase the likelihood of accurate indication of actual performance setting of the implant. The tools and methods according to the present solution guide a user towards precise adjustment of the setting of an adjustable implant such as a programmable shunt valve device. In this respect, a positioning tool 800 according to the present solution is shown in FIGS. 16 and 16A having a body 802 defining a centrally located access hole 804, intended to be directly positioned over the implant with bottom surface 801 resting against the skin of a patient, into which fits an adjustment tool 810, FIGS. 18 and 18A, having a body 816 and a handle 818 suitable for gripping by a thumb and a finger of a user wearing gloves, or between two gloved fingers of the user, to enable manipulation of adjustment tool 810 as described in more detail below.

Preferably, mechanical interference between the dimensions of the hole 804 and the adjustment tool 810, which in some constructions is enhanced by a rib, a ridge, or another feature on the periphery of at least one of the hole 804 and body 816 of adjustment tool 810, would limit the inward travel of the adjustment tool 810 to minimize or avoid protrusion beneath the positioning tool 800. It is also desirable to maintain alignment of the adjustment tool 810 if the implant were to protrude into the hole 804 to bring the patient's skin in contact with the adjustment tool 810.

The positioning tool 800 also defines a storage cavity 806 to hold the adjustment tool 810 and, preferably, with a material such as nickel iron alloy to contain, that is, to absorb and redirect, the magnetic flux emanating from the magnets 812 and 814 within body 816 while adjustment tool 810 is not being utilized. This storage, preferably with shielding, is intended as a safe place for the magnets 812 and 814, so that they do not interfere with the magnetic field sensing capability of the positioning tool 800, which is described in more detail below. The terms "magnet" and "magnets" as utilized herein include metals and alloys having properties of attracting or repelling iron as well as electromechanical mechanisms for generating similar magnetic fields.

Figure 17:
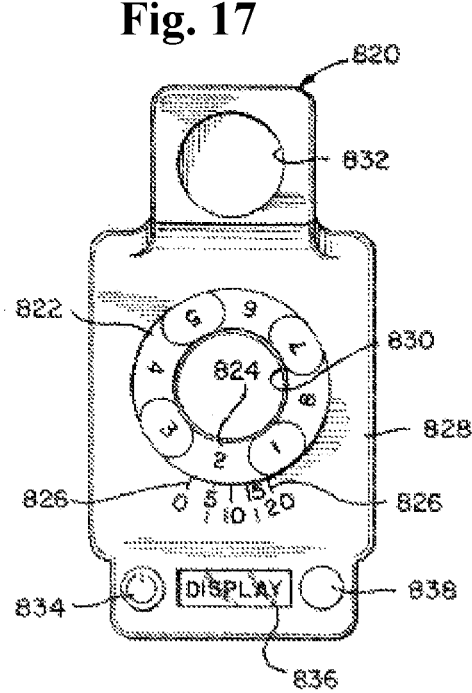
FIGS. 17 and 17A are schematic top and side views of an alternative positioning tool according to the present invention.

Positioning tool 800 includes a display 803 in this construction to enable the user to select the mode of operation and to provide visual feedback to the user. Also included is a power button 805 and a selection button 807 to enable the user to navigate the through menu driven options. Internal circuitry and an energy source such as a battery are also contained within body 802 in this construction. An alternative positioning tool 820, FIGS. 17 and 17A includes a moveable bezel 822 with the numbers 1 through 8 corresponding to the implant settings, an indicator mark 824 on setting #2, and indications 826 of degrees on body 828 of tool 820, shown in FIG. 17 in five degree increments from zero to twenty degrees. These could be used in the optimize tool orientation method described below as an alternative procedure where the first and/or second RC (Rotational Construct, also referred to as rotor 120) orientations are utilized and/or magnets or coils in bezel 822 can be adjusted, such as by manual movement, to achieve proper settings of valve 10. As one example, the user moves magnets or coils in the bezel 822 so the mark 824 on the center of setting 2 is at a predetermined angle (e.g. 5 degrees mark) on body 828. The body 828 further defines an access hole 830, an adjustment tool storage recess 832, a power button 834, a display 836, and a mode selection button 838 in this construction.

Figure 17A:
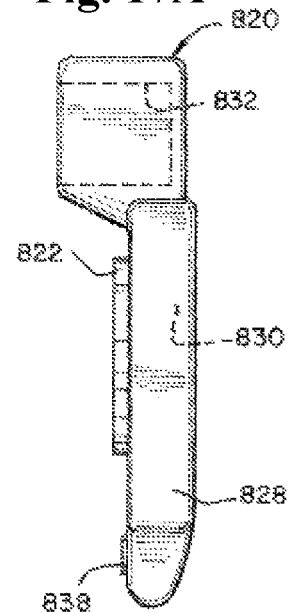
Figure 19:
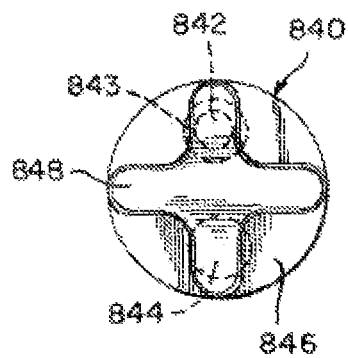
FIGS. 19 and 19A are schematic top and side views of an alternative adjustment tool for use with the positioning tool of FIG. 17.
Figure 19A:
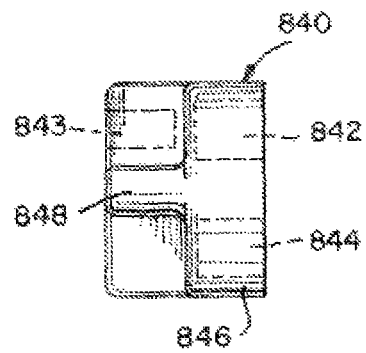
Figure 20A:
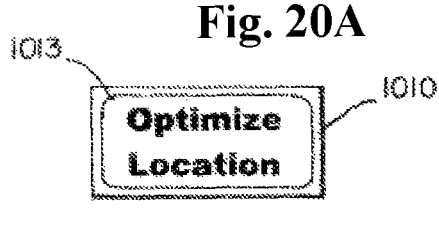
FIGS. 20A and 20B are examples of displayed mode and guidance to a user, respectively, for the display screens shown in FIGS. 16 and 17.
Figure 20B:
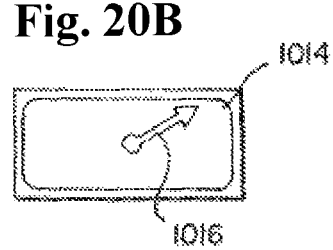

An adjustment tool 840, FIGS. 19-19A, includes an additional magnet 843, located in handle 848 on the opposite end to magnets 842 and 844 within body 846, to facilitate moving the RC during the process described below in relation to FIG. 21 wherein the adjustment tool 840 is inverted and rotated, while exposing the single pole magnetic field of magnet 843 to the implant. Recess 832 is sufficiently deep, as shown in FIG. 17A, to store adjustment tool 840 and, preferably, contain (absorb and redirect) magnetic flux so as to shield the magnetic field of adjustment tool 840 from other components of positioning tool 820.

In FIG. 21, the user may estimate a RC position setting. Having estimated the RC setting, the user may activate magnets and/or magnetic coils of the tool to either move the magnet and/or coil in the clockwise extreme of a respective pocket or the counter-clockwise extreme of the pocket. In one construction, the maximum angular range of RC movement within a pocket can be approximately 34 degrees for an implant having eight performance settings. One specialized tool for accomplishing the "pocket check" range of RC movement is adjustment tool 840, FIGS. 19-19A, with additional "checking" single magnet 843. A magnetic image of the valve setting may then be taken and then the valve setting may be determined from the image taking into account the RC's controlled position in either the clockwise or counterclockwise extreme of the pocket.

Any of the herein disclosed adjustment and/or positioning tools can include circumferentially and/or peripherally distributed magnets and/or coils as described with regards to tool 700/700a for use in the method and implementations of FIGS. 21-23 by disclosing tools and solutions for moving the rotor 120 inside its setting pocket to a defined position in order to eliminate the need for an accurate determination of the implanted valve flow direction during valve programmation. This in turn will allow for a very reliable determination of the current valve setting and setting change even with instruments of limited accuracy.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A setting adjustment tool for a magnetically adjustable device implanted in a patient, the magnetically adjustable device including a housing with a rotor having an axis of rotation and at least one rotor magnet, the rotor having a range of arcuate motion within each of a plurality of selectable performance settings, and wherein the rotor has an axle which turns about the axis of rotation, the setting adjustment tool comprising:
   a circumference;
   a plurality of magnetic coils, each coil circumferentially distributed a predetermined angular distance on the circumference of the setting adjustment tool;

wherein each magnetic coil is operable to activate and attract or repulse the at least one rotor magnet;

wherein a first coil of the plurality of magnetic coils is activatable for causing the at least one rotor magnet to move the rotor away from the first coil;

wherein a second coil of the plurality of magnetic coils is activatable for causing the at least one rotor magnet to move the rotor next to the second coil;

wherein a third coil of the plurality of magnetic coils is activatable for causing the at least one rotor magnet to move the rotor to a pocket of the magnetically adjustable device between second and third coils.

2. The tool of claim 1, wherein the predetermined angular distance ranges between 40 mm and 50 mm.

3. The tool of claim 1, wherein one of the magnetic coils is movable between the extreme counterclockwise and clockwise positions of the circumference and capable of adjusting the device from a constrained condition setting to an unconstrained condition setting.

4. The tool of claim 1, wherein at least one of the magnetic coils is movable, and the plurality of magnetic coils include at least eight coils each equally distributed the predetermined angular distance on the circumference.

5. The tool of claim 1, wherein each magnetic coil is formed by a pair of magnetic coils disposed adjacent the other, each coil of each pair being angularly oriented together by sharing a common edge or corner with respect to the other coil of the pair and circumferentially distributed about the circumference of the tool and relative to an associated lock stop of the housing.

6. The tool of claim 5, wherein each coil of each pair is selectively angled at a predetermined angle that is approximately 45 degrees relative to each adjoining edge of the respective coil.

7. The tool of claim 1, wherein the magnetic coils are positioned on the circumference and are capable of attracting or repulsing the at least one magnet of the rotor in a radial direction by at least a predetermined angle within a plane of rotation of the at least one magnet thereby inducing a rotating moment into the rotor.

8. A setting adjustment system for a magnetically adjustable device implanted in a patient, the system comprising:

the magnetically adjustable device including a housing and a rotor having an axis of rotation and at least one rotor magnet, the rotor having a range of arcuate motion within each of a plurality of selectable performance settings, and wherein the rotor has an axle which turns about the axis of rotation;

a setting adjustment tool operatively connected to the magnetically adjustable device, the tool comprising:

a circumference and a plurality of magnetic coils circumferentially distributed on the circumference;

wherein each magnetic coil is operable to activate and attract or repulse the at least one rotor magnet;

wherein a first coil of the plurality of magnetic coils is activatable for causing the at least one rotor magnet to move the rotor away from the first coil;

wherein a second coil of the plurality of magnetic coils is activatable for causing the at least one rotor magnet to move the rotor next to the second coil;

wherein a third coil of the plurality of magnetic coils is activatable for causing the at least one rotor magnet to move the rotor to a pocket of the magnetically adjustable device between the second and the third coils;

wherein at least one of the magnetic coils is movable along the circumference between a plurality of predetermined positions associated with the selectable performance settings.

9. The system of claim 8, wherein the plurality of magnetic coils are magnetic coil pairs, each coil of each pair being angularly oriented together and circumferentially distributed about the circumference of the tool and relative to an associated lock stop of the housing;

wherein each of the first, second, and third magnetic coil pairs are operable to radially attract or repulse the at least one rotor magnet;

wherein activating each magnetic coil pair of the adjustment tool attracts or repulses the at least one magnet of the rotor in a radial direction by at least a predetermined angle within a plane of rotation of the at least one magnet thereby inducing a rotating moment into the rotor.

10. The system of claim 9, wherein the predetermined angle is approximately 45 degrees.

11. The system of claim 8, wherein the pocket is defined between one of a plurality of predetermined opposite lock stops of the housing and are associated with the selectable performance settings.

12. The system of claim 8, wherein one of the magnetic coils is movable between the extreme counterclockwise and clockwise positions of the circumference and capable of adjusting the magnetically adjustable device from a constrained condition setting to an unconstrained condition setting.

13. The system of claim 8, wherein at least one of the magnetic coils is movable, and the plurality of magnetic coils include at least eight coils each equally distributed on the circumference.

14. The system of claim 8, wherein each magnetic coil is formed by a pair of magnetic coils disposed adjacent the other, each coil of each pair being angularly oriented together by sharing a common edge or corner with respect to the other coil of the pair and circumferentially distributed about the circumference of the tool and relative to an associated lock stop of the housing.

* * * * *